United States Patent
May et al.

(10) Patent No.: US 6,927,233 B1
(45) Date of Patent: Aug. 9, 2005

(54) 5HT2 AGONISTS FOR CONTROLLING IOP AND TREATING GLAUCOMA

(75) Inventors: Jesse A. May, Fort Worth, TX (US); Anura P. Dantanarayana, Fort Worth, TX (US)

(73) Assignees: Alcon, Inc., Hunenberg (CH); Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/221,458

(22) PCT Filed: Nov. 14, 2000

(86) PCT No.: PCT/US00/31246

§ 371 (c)(1),
(2), (4) Date: Mar. 11, 2003

(87) PCT Pub. No.: WO01/70207

PCT Pub. Date: Sep. 27, 2001

Related U.S. Application Data

(60) Provisional application No. 60/190,288, filed on Mar. 17, 2000.

(51) Int. Cl.[7] .............................................. A61K 31/415
(52) U.S. Cl. ....................... 514/403; 514/405; 514/912; 514/913
(58) Field of Search ................... 514/403, 405

(56) References Cited

U.S. PATENT DOCUMENTS

| 3,994,890 A | * | 11/1976 | Fujimura et al. ........... 544/132 |
| 4,690,931 A | | 9/1987 | Wick et al. |
| 5,151,444 A | | 9/1992 | Ueno et al. |
| 5,296,504 A | | 3/1994 | Stjernschantz et al. |
| 5,352,708 A | | 10/1994 | Woodward et al. |
| 5,422,368 A | | 6/1995 | Stjernschantz et al. |
| 5,889,052 A | | 3/1999 | Klimko et al. |
| 6,664,286 B1 | * | 12/2003 | May et al. .................. 514/415 |

FOREIGN PATENT DOCUMENTS

| WO | WO 94/13275 A1 | | 6/1994 |
| WO | WO 98/30548 A1 | | 7/1998 |
| WO | WO 00/16761 | * | 3/2000 |
| WO | WO 01/40183 A1 | | 6/2001 |

OTHER PUBLICATIONS

Osborne, Neville N., "Serotonin and melatonin in the iris/ciliary processes and their involvement in intraocular pressure", ACTA Neurobiol. Exp., 54 (Suppl.) 57–64 (1994).

\* cited by examiner

*Primary Examiner*—Frederick Krass
(74) *Attorney, Agent, or Firm*—Kilyk & Bowersox, P.L.L.C.

(57) ABSTRACT

Compositions and methods for controlling intraocular pressure and treating glaucoma using 1-(2-aminopropyl)-indazol-6-ol are disclosed.

6 Claims, No Drawings

5HT2 AGONISTS FOR CONTROLLING IOP AND TREATING GLAUCOMA

This application claims priority from PCT/US00/42356 filed on November 14, 2000, which claims the benefit of U.S. Ser. No. 60/190,288, filed on Mar. 17, 2000.

The present invention is directed to the use of 1-(2-aminopropyl)-indazol-6-ol for lowering and controlling intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be a high risk for the eventual development of the visual loss associated with glaucoma. Some patients with glaucomatous field loss have relatively low intraocular pressures. These so called normotension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

The compound, 1-(2-aminopropyl)-indazol-6-ol, is disclosed in WO98/30548. Example 46 within the application discloses the S-enantiomer of 1-(2-aminopropyl)-indazol-6-ol. The utility cited in the application is for treating central nervous system diseases, such as, sexual disorders, genital insufficiency, appetite regulation disorders, anxiety, depression, and sleep disorders. No ophthalmic indications are disclosed.

SUMMARY OF THE INVENTION

The present invention is directed to compositions of 1-(2-aminopropyl)-indazol-6-ol and its use for lowering and controlling IOP and treating glaucoma.

DESCRIPTION OF PREFERRED EMBODIMENTS

Surprisingly, it has been found that 1-(2-aminopropyl)-indazol-6-ol ("Compound") and its S-(+)-isomer, when dosed at 300 μg, in the lasered monkey model of ocular hypertension causes a significant decrease in IOP as shown in the table set forth below. Intraocular pressure was determined with an Alcon Pneumatonometer after light corneal anesthesia with 0.1% proparacaine. Eyes were washed with saline after-each measurement. After a baseline IOP measurement, test compound was instilled in one 30 μL aliquot to the right eyes only of nine cynomolgus monkeys. Vehicle was instilled in the right eyes of six additional animals. Subsequent IOP measurements were taken at 1, 3, and 6 hours. A compound is considered efficacious in this model of ocular hypertension if there is a decrease in the baseline IOP of the lasered eye (O.D.) of at least 20% following topical administration.

IOP Response to 1-(2-Aminopropyl)-indazol-6-ol and its S(+)-isomer

|  | Dose | Baseline IOP | IOP Response % Change (ΔmmHg) | | |
| --- | --- | --- | --- | --- | --- |
|  | (μg) | (mmHg) | 1 hr | 3 hr | 6 hr |
| Compound | 300 | 40.1 | −17.6 (7.3) | −28.1 (11.8) | −33.8 (14.6) |
|  | vehicle | 40.5 | −6.5 (3.0) | −13.6 (5.7) | −8.1 (3.8) |
| S-(+)-isomer | 300 | 40.3 | −15.0 (6.4) | −35.3 (14.8) | −40.8 (17.1) |
|  | vehicle | 38.0 | −3.1 (1.8) | −6.8 (3.3) | −4.7 (2.8) |

The S-isomer of 1-(2-aminopropyl)-indazol-6-ol is the preferred isomer for lowering and controlling IOP and treating glaucoma.

The Compound can be incorporated into various types of ophthalmic formulations for delivery to the eye (e.g., topically, intracamerally, or via an implant). It is preferably incorporated into topical ophthalmic formulations for delivery to the eye. The Compound may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving the Compound in a physiologically acceptable isotonic aqueous buffer. Further, the ophthalmic solution may include an ophthalmologically acceptable surfactant to assist in dissolving the Compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the Compound is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The Compound is preferably formulated as a topical ophthalmic suspension or solution, with a pH of about 5 to 8. The Compound will normally be contained in these formulations in an amount 0.01% to 5% by weight, but preferably in an amount of 0.1% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), α1 antagonists (e.g. nipradolol), α2 agonists (e.g., iopidine and brimonidine), miotics (e.g., pilocarpine and epinephrine), prostaglandin analogs (e.g., latanoprost, travaprost, unoprostone, and compounds set forth in U.S. Pat. Nos.

5,889,052; 5,296,504; 5,422,368; and 5,151,444, "hypotensive lipids" (e.g., lumigan and compounds set forth in 5,352,708), and neuroprotectants (e.g., compounds from U.S. Pat. No. 4,690,931, particularly eliprodil and R-eliprodil, as set forth in a pending application U.S. patent application Ser. No. 06/203350, now U.S. Pat. No. 4,239,876, and appropriate compounds from WO94/13275, including memantine.

The following topical ophthalmic formulations are useful according to the present invention administered 1–4 times per day according to the discretion of a skilled clinician.

EXAMPLE 1

| Ingredients | Amount (wt %) |
| --- | --- |
| 1-(2-Aminopropyl)-indazol-6-ol (S-(+)-isomer) | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 2

| Ingredients | Amount (wt %) |
| --- | --- |
| 1-(2-Aminopropyl)-indazol-6-ol | 0.01–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 3

| Ingredients | Amount (wt %) |
| --- | --- |
| 1-(2-Aminopropyl)-indazol-6-ol (S-(+)-isomer) | 0.01–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 4

| Ingredients | Amount (wt %) |
| --- | --- |
| 1-(2-Aminopropyl)-indazol-6-ol | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |

We claim:

1. A method for lowering or controlling intraocular pressure or treating glaucoma which comprises administering a composition comprising a pharmaceutically effective amount of 1-(2-aminopropyl)-indazol-6-ol to a subject in need thereof.

2. The method of claim 1 wherein the 1-(2-aminopropyl)-indazol-6-ol is the S(+) isomer.

3. The method of claim 1 wherein the composition is an ophthalmic formulation in which the 1-(2-aminopropyl)-indazol-6-ol is present at a concentration of from 0.01 to 5 weight percent.

4. The method of claim 3 wherein the concentration is 0.1 to 2 weight percent.

5. The method of claim 2 wherein the composition is an ophthalmic formulation in which the S-(+)-isomer of 1-(2-aminopropyl)-indazol-6-ol is present at a concentration of from 0.01 to 5 weight percent.

6. The method of claim 5 wherein the concentration is from 0.1 to 2 weight percent.

* * * * *